United States Patent
Modak et al.

(10) Patent No.: US 6,503,952 B2
(45) Date of Patent: *Jan. 7, 2003

(54) TRIPLE ANTIMICROBIAL COMPOSITION

(75) Inventors: Shanta Modak, River Edge, NJ (US); Lester Sampath, Nyack, NY (US); Lauserpina A. Caraos, Hollis, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/758,930

(22) Filed: Jan. 11, 2001

(65) Prior Publication Data

US 2001/0016589 A1 Aug. 23, 2001

Related U.S. Application Data

(63) Continuation of application No. 09/028,552, filed on Feb. 24, 1998, now abandoned, which is a continuation-in-part of application No. 09/011,841, filed as application No. PCT/US96/18104 on Nov. 12, 1996, now Pat. No. 5,985,931, which is a continuation-in-part of application No. 08/556,256, filed on Nov. 13, 1995, now Pat. No. 5,705,532.

(51) Int. Cl.⁷ ..................... A61K 31/155; A61K 31/14; A61K 31/05
(52) U.S. Cl. ................ 514/635; 514/643; 514/737
(58) Field of Search ................. 514/635, 643, 514/737

(56) References Cited

U.S. PATENT DOCUMENTS

| | | |
|---|---|---|
| 3,063,895 A | 11/1962 | Pearson et al. |
| 3,468,898 A | 9/1969 | Cutler et al. |
| 3,506,720 A | 4/1970 | Model et al. |
| 3,639,632 A | 2/1972 | McNamara et al. |
| 3,671,644 A | 6/1972 | Irani et al. |
| 4,022,834 A | 5/1977 | Gundersen |
| 4,022,911 A | 5/1977 | Goldhaft et al. |
| 4,053,636 A | 10/1977 | Eustis, III et al. |
| 4,125,628 A | 11/1978 | Goldhaft et al. |
| 4,134,971 A | 1/1979 | Inoue et al. |
| 4,198,392 A | 4/1980 | Juneja |
| 4,290,846 A | 9/1981 | Muntwyler |
| 4,321,257 A | 3/1982 | Sipos |
| 4,420,484 A | 12/1983 | Gorman et al. |
| 4,486,405 A | 12/1984 | Klein |
| 4,900,721 A | 2/1990 | Bansemir et al. |
| 4,990,329 A | 2/1991 | Sampathkumar |
| 5,017,617 A | 5/1991 | Kihara et al. |
| 5,030,659 A | 7/1991 | Bansemir et al. |
| 5,122,541 A | 6/1992 | Eggensperger et al. |
| 5,244,666 A | 9/1993 | Murley |

FOREIGN PATENT DOCUMENTS

WO      9526134      10/1995

OTHER PUBLICATIONS

Larson and Bobo, 1992, J. Emergency Med. 10:7–11.

*Primary Examiner*—Rebecca Cook
(74) *Attorney, Agent, or Firm*—Baker Botts LLP

(57) ABSTRACT

An antimicrobial composition comprising (i) between 0.025 and 2 percent of an antimicrobial agent selected from the group consisting of chlorhexidine free base, a chlorhexidine salt, polyhexamethylene biguanide, and alexidine; (ii) between 0.005 and 0.1 percent of a quaternary ammonium compound; and (iii) between 0.025 and 2 percent of a chlorinated phenol compound.

16 Claims, No Drawings

TRIPLE ANTIMICROBIAL COMPOSITION

This application is a continuation of prior application Ser. No. 09/028,552 filed Feb. 24, 1998, now abandoned which is a continuation-in-part of prior application Ser. No. 09/011,841 filed Jun. 2, 1998, now issued as U.S. Pat. No. 5,985,931, which is a national phase application pursuant to 35 U.S.C. 371 of international application No. PCT/US96/18104 filed Nov. 12, 1996, which is a continuation-in-part of application Ser. No. 08/556,256 filed Nov. 13, 1995, now issued as U.S. Pat. No. 5,705,532.

INTRODUCTION

The present invention relates to antimicrobial compositions comprising a biguanide compound, a chlorinated phenol compound, and a quaternary ammonium compound. It is based, at least in part, on the discovery that combinations of biguanide, a chlorinated phenol compound such as parachlorinated phenol compound such as parachlorometaxylenol or triclosan, and a quaternary ammonium compound exhibit synergistic antimicrobial activity.

BACKGROUND OF THE INVENTION

The antimicrobial agents chlorhexidine ("CHX"; 1,6 bis ($N^5$-p-chlorophenyl-$N^1$-biguanido)hexane), benzalkonium chloride ("BZK") and parachlorometaxylenol ("PCMX") have been used, individually, in antimicrobial compositions. For example, the well-known antiseptic scrubs HIBICLENS®, ULTRADEX® and TECHNI-CARE® contain 4% CHX (HIBICLENS®) and 3% PCMX (ULTRADEX® and TECHNICARE®). The use of these scrubs, however, provides less than optimal antimicrobial protection, in that neither scrub is believed to be fully effective in rapidly inactivating pathogens or in reducing skin flora for an extended period of time. Furthermore, the relatively high levels of antimicrobial agents in these preparations are frequently associated with skin irritation.

Compositions which combine one or more of the foregoing antimicrobial agents with additional compounds are also known, as illustrated by the following references.

U.S. Pat. No. 5,244,666 by Murley, issued Sep. 14, 1993 ("the '666 patent") relates to an antiseptic scrub and wound disinfectant wherein a quaternary ammonium compound and a substituted phenolic compound are combined to produce enhanced antimicrobial activity at lower concentrations. The '666 patent states that the use of such combinations, together with degreasing emulsifiers, detergents, skin softeners and soothing agents is new. The compositions comprise about 3% (wt/wt) of a quaternary ammonium compound and about 3% of a substituted phenolic compound.

U.S. Pat. No. 5,030,659 by Bansemir et al., issued Jul. 9, 1991 ("the '659 patent") relates to disinfectant compositions comprising a quaternary ammonium compound, a biguanide, and a phenolic compound. The antimicrobial agent present in greatest concentration is the quaternary ammonium compound; the working examples of the '659 patent include compositions comprising 15–20% of the quaternary ammonium compound BZK.

U.S. Pat. No. 4,900,721 by Bansemir et al., issued Feb. 13, 1990, relates to liquid, aqueous disinfectants based on alcohol and hydrogen peroxide which comprise one or more $C_2$–$C_8$ alcohols, hydrogen peroxide (or a compound which produces hydrogen peroxide), one or more carboxylic acids, one or more microbicidally active nitrogen-containing organic compounds (e.g., CHX or BZK), and one or more microbicidally active phenolic compounds (including polychlorinated xylenes).

U.S. Pat. No. 4,420,484 by Gorman et al., issued Dec. 13, 1983, relates to combinations of antimicrobial agents (such as CHX or BZK) with polyethylene glycol surfactant and betaine or amine oxide surfactant.

U.S. Pat. Nos. 4,125,628 and 4,022,911, by Goldhaft et al., issued Nov. 14, 1978 and May 10, 1977, respectively, relate to combinations of a quaternary ammonium compound, a phenol or derivative thereof, and formaldehyde.

U.S. Pat. No. 3,639,632 by McNamara et al., issued Feb. 1, 1972, relates to a synergistic antimicrobial composition containing 1,1'-hexamethylenebis [5-(2-ethylhexyl) biguanide] dihydrochloride and 4-chloro-2-hydroxyphenyl, 2,4-dichlorophenyl ether.

Larson et al., 1992, J. Emergency Med. 10: 7–11 discloses that in the presence of blood, topical antimicrobial products containing alcohol were associated with greater initial reductions in colonizing flora.

The number of antimicrobial preparations which have been developed illustrates the continuing search for a composition that rapidly and effectively provides antimicrobial activity without substantial adverse effects, such as skin irritation.

SUMMARY OF THE INVENTION

The present invention relates to antimicrobial compositions comprising a biguanide compound, a chlorinated phenol compound, and a quaternary ammonium compound. The antimicrobial compositions of the invention may be utilized in antimicrobial detergents, soaps, creams, wipes, rinses and emulsions for use in the medical community as well as general public use.

In particular non-limiting embodiments of the invention, the chlorinated phenol compound is parachlorometaxylenol or triclosan.

In specific, nonlimiting embodiments of the invention, the present invention relates to antimicrobial compositions comprising (i) between 0.025 and two percent (all ranges herein being inclusive of their limits) by weight biguanide; (ii) between 0.005 and 0.1 percent by weight of a quaternary ammonium compound; and (iii) between 0.025 and two percent by weight of a chlorinated phenol compound.

DETAILED DESCRIPTION OF THE INVENTION

The present invention relates to antimicrobial compositions comprising a biguanide compound, a chlorinated phenol compound, and a quaternary ammonium compound.

Biguanide compounds which may be used according to the invention include but are not limited to the following: chlorhexidine free base, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine diiodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, polyhexamethylene biguanide ("PHMB"), and alexidine (N,N"-Bis(2-ethylhexyl)-3,12-diimino-2,4,11,13-tetraazatetradecanediimidamine; 1,1'hexamethyl-enebis [5-(2-ethylhexyl)biguanide]).

Quaternary ammonium compounds that may be used according to the invention include, but are not limited to, benzalkonium chloride (BZK), benzethonium chloride, other benzalkonium or benzethonium halides, cetylpyridinium chloride, dequalinium chloride, N-myristyl-N-methylmorpholinium methyl sulfate, poly[N-[3-(dimethylammonio)propyl]-N'-[3-(ethyleneoxyethelene dimethylammonio)propyl]urea dichloride], alpha-4-[1-tris(2-hydroxyethyl)ammonium chloride-2-butenyl]-omega-tris(2-hydroxyethyl)ammonium chloride, alpha4-[1-tris(2-hydroxyethyl)ammonium chloride-2-butenyl]poly[1-dimethyl ammonium chloride-2-butenyl]-omega-tris(2-hydroxyethyl)ammonium chloride, poly[oxyethylene(dimethyliminio)ethylene(dimethyliminio)-ethylene dichloride], ethyl hexadecyl dimethyl ammonium ethyl sulfate, dimethyl ammonium ethyl sulfate, dimethylethylbenzyl ammonium chloride, dimethylbenzyl ammonium chloride, cetyldimethylethyl ammonium bromide, and organosilicon-substituted quaternary ammonium compounds such as 3-(trimethoxysilyl propyloctadecyldimethyl ammonium chloride.

Chlorinated phenol compounds which may be used according to the invention include but are not limited to parachlorometaxylenol, triclosan (2,4,4'-trichloro-2 hydroxy di-phenyl ether), 2-chlorophenol, 3-chlorophenol, 4-chlorophenol, 2,4-dichlorophenol, 2,4,6-trichlorophenol, 2,3,4,6-tetrachlorophenol, pentachlorophenol, 4-chlororesorcinol, 4,6-dichlororesorcinol, 2,4,6-trichlororesorcinol, alkylchlorophenols (including p-alkyl-o-chlorophenols, o-alkyl-p-chlorophenols, dialkyl-4-chlorophenol, and tri-alkyl-4-chlorophenol), dichloro-m-xylenol, chlorocresol, o-benzyl-p-chlorophenol, 3,4,6-trichlorphenol, 4-chloro-2-phenylphenol, 6-chloro-2-phenylphenol, o-benzyl-p-chlorophenol, and 2,4-dichloro-3, 5-diethylphenol. It may be preferred to utilize triclosan for certain applications, as it subjectively has less of an offensive odor. Further, chlorhexidine free base and triclosan form a complex which remains on surfaces for a longer period of time, thereby providing long term antimicrobial activity.

In specific, nonlimiting embodiments of the invention, the present invention relates to antimicrobial compositions comprising (i) between 0.025 and two percent by weight biguanide; (ii) between 0.005 and 0.1 percent by weight of a quaternary ammonium compound; and (iii) between 0.025 and two percent by weight of a chlorinated phenol compound.

In a preferred, nonlimiting embodiment of the invention, where the composition is to be used as an antimicrobial scrub, the concentration of biguanide may be between one and two percent (unless indicated otherwise, all percentages herein refer to percentages by weight). In alternate nonlimiting embodiments of the invention, the concentration of biguanide may be between 0.05 and 0.1 percent by weight, and, in specific embodiments, equal to 0.05 percent or 0.1 percent by weight. Where the biguanide is PHMB, its concentration may preferably be between 0.025 and 0.1 percent.

In preferred, nonlimiting embodiments of the invention, wherein the composition is to be used as an antimicrobial scrub, the concentration of quaternary ammonium compound, such as benzalkonium chloride, may be between 0.005 and 0.1 percent. In alternative embodiments, the concentration of quaternary ammonium compound, such as benzalkonium chloride, may be between 0.005 and 0.01 percent.

In preferred, nonlimiting embodiments of the invention, wherein the composition is to be used as an antimicrobial scrub, the concentration of chlorinated phenol compound may be between 0.025 and 2 percent. In alternative embodiments, the concentration of chlorinated phenol compound may be between 0.05 and 0.25 percent or between 0.025 and 0.1 percent.

In one specific, nonlimiting embodiment, the present invention provides for an antimicrobial composition comprising (i) between 0.05 and 0.1 percent of an antimicrobial agent selected from the group consisting of chlorhexidine free base, a chlorhexidine salt, polyhexamethylene biguanide, and alexidine; (ii) between 0.005 and 0.1 percent of a quaternary ammonium compound; and (iii) between 0.025 and 0.1 percent of a chlorinated phenol compound. In a preferred nonlimiting embodiment, the antimicrobial agent is chlorhexidine free base, the quaternary ammonium compound is benzalkonium chloride, and the chlorinated phenol compound is triclosan.

The compositions of the invention may further comprise an organic solvent that aids in the dissolution of the antimicrobial agents, for example, isopropanol or propylene glycol. The amount of isopropanol in the compositions of the invention is preferably between 2.5 and 5 percent by weight. In specific preferred embodiments, the amount of isopropanol is 5 percent by weight.

In yet another embodiment, the present invention provides for a scrub base that is believed to enhance the effectiveness of antimicrobial agents. This base comprises 10–15 percent of a pluronic copolymer surfactant, including but not limited to pluronic F87; 1–5 percent of an amine oxide foaming agent, including but not limited to limited to, glucamate DOE 120; one or more antimicrobial agent; and water, wherein the pH has been adjusted to 5.5–6.0 with a mild acid such as, but not limited to, gluconolactone, lactic acid, salicvlic acid, citric acid or gluconic acid. Suitable antimicrobial agents include, but are not limited to, parachlorometaxylenol, phenoxyethanol, povidone iodine, chlorhexidine or a chlorhexidine salt, benzalkonium chloride, and combinations thereof. Compounds such as isopropanol or propylene glycol may also be used to improve the solubility of antimicrobial agent.

It has surprisingly been found that, contrary to the teachings of the prior art, a non-ionic surfactant such as Pluronic F87 is compatible with parachlorometaxylenol. The prior art generally teaches the use of amphoteric or anionic surfactants in parachlorometaxylenol formulations.

The compositions of the invention may be incorporated into a variety of products, including, but not limited to hand disinfectants, hand soaps, topical creams, antiseptic rinses or soaks, and antiseptic wipes/towelettes. Likewise, they may be incorporated as preservatives, for example, in cosmetics.

Such products may be prepared according to methods known in the art. The present invention provides for the following specific, preferred, nonlimiting embodiments:

The present invention provides for an antimicrobial scrub having a ratio of ingredients as in the following composition: 2 grams parachlorometaxylenol; 2 grams chlorhexidine digluconate; 0.1 gram benzalkonium chloride; 5.0 ml isopropanol; 12.5 grams pluronic F87; 1.8 grams lauryl dimethylamine oxide; 0.25 grams glucamate DOE; 1 gram D-glucanolactone; and 75.35 grams deionized water; wherein the pH is adjusted to between 5.5–6.0 with D-glucanolactone. In related embodiments, 2–10 percent cocamidopropyl betaine may be added to the above-identified composition.

In another related embodiment, the present invention provides for an antimicrobial scrub having a ratio of ingredients as in the following composition: 2 grams parachlorometaxylenol; 2 grams chlorhexidine digluconate; 0.1 gram benzalkonium chloride; 10 grams propylene glycol; 12.5 grams pluronic F87; 1.8 grams lauryl dimethylamine oxide; 0.25 grams glucamate DOE; 1 gram D-glucanolactone; and 75.35 grams deionized water; wherein the pH is adjusted to between 5.5–6.0 with D-glucanolactone. In related embodiments, 2–10 percent cocamidopropyl betaine may be added to the above-identified composition.

In yet another nonlimiting specific embodiment, the present invention provides for a topical cream comprising chlorhexidine free base or salt, triclosan, phenoxyethanol, and benzalkonium chloride. Preferably, the concentrations of the compounds are 0.025 percent chlorhexidine, 0.05 percent triclosan, 0.25 percent phenoxyethanol and 0.005 percent benzalkonium chloride.

In yet another nonlimiting specific embodiment, the present invention provides for a topical cream comprising chlorhexidine salt, parachlorometaxylenol, phenoxyethanol and benzalkonium chloride. Preferably, the cholrhexidine salt is chlorhexidine gluconate, and the concentrations are 0.025 percent chlorhexidine gluconate, 0.125 percent parachlorometaxylenol, 0.025 percent phenoxyethanol, and 0.005 percent benzalkonium chloride.

In yet another nonlimiting specific embodiment, the present invention provides for a disinfectant wipe comprising polyhexamethylene biguanide, triclosan, benzalkonium chloride and phenoxyethanol. Preferably, the concentration of polyhexamethylene biguanide is 0.2 percent, the concentration of triclosan is 0.1 percent, the concentration of benzalkonium chloride is 0.05 percent, and the concentration of phenoxyethanol is 0.1 percent.

In yet another nonlimiting specific embodiment, the present invention provides for an alcohol-based compositions comprising a biguanide compound, a chlorinated phenol compound, and a quaternary ammonium compound, wherein the alcohol content is between 50 and 90 percent and preferably about 70 percent.

The compositions of the invention may further comprise quaternaries such as isostearyl ethylimidonium ethosulfate ("ISIES"), polyoxyethylene dihydroxypropyl linoleaminium chloride ("SL-5"), and bishydroxyethyl dihydroxypropyl stearaminium chloride ("TG"), and phospholipids such as cocamidopropyl phosphatidyl PG-dimonium chloride ("PTC"), linoleamidopropyl phosphatidyl PG-dimonium chloride ("EFA"), and stearamidopropyl phosphatidyl PG-dimonium chloride and cetyl alcohol ("SV"), obtainable from Mona Industries, Paterson, New Jersey.

The usefulness of the present invention is demonstrated by the following examples, set forth as examples only, and not by way of limitation. It should be noted that the concentrations of active agents are lower than those used in currently available products, thereby diminishing the risk of skin irritation, but providing effective antimicrobial protection.

EXAMPLE

Synergism of PCMX, CHX and BZK

Table 1 shows the results when various concentrations of PCMX in 2.5% isopropanol ("ISOPR") were exposed to *Staphylococcus aureus* bacteria. To produce each sample, 0.1 ml of a ten-fold concentrated antimicrobial solution was added to 0.9 ml of TSB broth containing 20% serum and $10^7$ colony forming units (CFU) of *Staphylococcus aureus*. After one minute, a 50 microliter aliquot from each sample was diluted to a volume of 10 ml with LTSB drug inactivating medium (5% Tween 80, 2% lecithin, 0.6% sodium oleate, 0.5% sodium thiosulfate, 0.1% protease peptone and 0.1% tryptone), and then 0.5 ml of the diluted culture was plated on trypticase soy agar plates. The plates were incubated at 37° C. for 24 hours, and then colony counts per milliliter of the original 1 ml antimicrobial containing culture were determined.

TABLE 1

| Sample | A1 | B1 | C1 | D1 | E1 | F1 |
|---|---|---|---|---|---|---|
| % PCMX | 0 | .01 | .02 | .03 | .04 | .05 |
| % ISOPR | 2.5 | 2.5 | 2.5 | 2.5 | 2.5 | 2.5 |
| CFU/ml | $1 \times 10^7$ | $8 \times 10^6$ | $4 \times 10^6$ | $3.5 \times 10^6$ | $1 \times 10^6$ | $1.8 \times 10^5$ |

Table 1 demonstrates that as the concentration of PCMX was increased from 0 to 0.05%, a reduction of CFU by approximately a factor of ten was observed.

Table 2 shows the results of experiments in which 0.05% chlorhexidine was added to the compositions tested in Samples A1-F1, as described in Table 1. The corresponding samples, containing 0.05% chlorhexidine, are designated A2-F2.

TABLE 2

| Sample | A2 | B2 | C2 | D2 | E2 | F2 |
|---|---|---|---|---|---|---|
| % PCMX | 0 | .01 | .02 | .03 | .04 | .05 |
| % CHX | .05 | .05 | .05 | .05 | .05 | .05 |
| % ISOPR | 2.5 | 2.5 | 2.5 | 2.5 | 2.5 | 2.5 |
| CFU/ml | $8 \times 10^6$ | $2 \times 10^5$ | $7 \times 10^4$ | $7 \times 10^3$ | 0 | 0 |

Table 2 demonstrates that 0.05% CHX, used alone, had very little effect on the number of CFU present in control sample A1 ($1 \times 10^7$ CFU), in that control sample A2 exhibited $8 \times 10^6$ CFU. Similarly, sample B1, which contained 0.01% PCMX, exhibited $8 \times 10^6$ CFU. However, the combination of 0.01% PCMX and 0.05% CHX in sample B2 resulted in an approximately 40-fold drop in the number of CFU relative to control A2 (to $2 \times 10^5$ CFU). Moreover, although 0.03% PCMX reduced the number of CFU by a factor of 3 relative to control A1 to $3.5 \times 10^6$ (sample D1), the combination of 0.03% PCMX and 0.05% CHX decreased the number of CFU by approximately a factor of 1000 relative to control A2 (to $7 \times 10^3$ CFU, sample D2). The combination of 0.04% PCMX and 0.05% CHX eliminated all CFU (sample E2). This data demonstrates the synergistic antimicrobial activity of PCMX and CHX, and is corroborated by data presented in Table 3, which combines the amount of PCMX contained in samples A1-F1 with 0.1% CHX, in corresponding samples A3-F3.

TABLE 3

| Sample | A3 | B3 | C3 | D3 | E3 | F3 |
|---|---|---|---|---|---|---|
| % PCMX | 0 | .01 | .02 | .03 | .04 | .05 |
| % CHX | .1 | .1 | .1 | .1 | .1 | .1 |
| % ISOPR | 2.5 | 2.5 | 2.5 | 2.5 | 2.5 | 2.5 |
| CFU/ml | $9 \times 10^5$ | $7 \times 10^4$ | $4 \times 10^4$ | $1.2 \times 10^3$ | 0 | 0 |

Experiments have also demonstrated the synergistic activity of BZK with PCMX and CHX. Table 4 shows the results of experiments in which 0.01% BZK was added to the compositions of samples A1 and B2-F2, thereby testing 0.01% BZK used alone or in combination with 0.05% CHX and 0.01–0.05% PCMX in samples A4-F4. Of note, a control sample for the samples set forth in Table 4, which contained 2.5% ISOPR and no antimicrobial, exhibited $1.2 \times 10^7$ CFU (not set forth in Table 4).

TABLE 4

| Sample | A4 | B4 | C4 | D4 | E4 | F4 |
|---|---|---|---|---|---|---|
| % PCMX | 0 | .01 | .02 | .03 | .04 | .05 |
| % CHX | 0 | .05 | .05 | .05 | .05 | .05 |
| % BZK | .01 | .01 | .01 | .01 | .01 | .01 |
| % ISOPR | 2.5 | 2.5 | 2.5 | 2.5 | 2.5 | 2.5 |
| CFU/ml | $4 \times 10^6$ | $8 \times 10^2$ | 0 | 0 | 0 | 0 |

Table 4 shows that despite the fact that 0.01% BZK alone (sample A4; $4 \times 10^6$ CFU) decreased the number of CFU by a factor of only 3 relative to the control sample ($1.2 \times 10^7$ CFU), and sample B2 (0.01% PCMX+0.05% CHX) decreased the number of CFU by a factor of approximately 40 relative to control A2, sample B4 (0.01% PCMX+0.05% CHX+0.01% BZK) exhibited an approximately 10,000-fold decrease in the number of CFU relative to control A4. This data demonstrates the synergistic anti-microbial activity of low concentrations of PCMX, CHX, and BZK, and is corroborated by the data presented in Table 5, which combines the same amounts of PCMX and CHX with 0.005% BZK in samples A5-F5.

TABLE 5

| Sample | A5 | B5 | C5 | D5 | E5 | F5 |
|---|---|---|---|---|---|---|
| % PCMX | 0 | .01 | .02 | .03 | .04 | .05 |
| % CHX | 0 | .05 | .05 | .05 | .05 | .05 |
| % BZK | .005 | .005 | .005 | .005 | .005 | .005 |
| % ISOPR | 2.5 | 2.5 | 2.5 | 2.5 | 2.5 | 2.5 |
| CFU/ml | $5 \times 10^6$ | $1.2 \times 10^3$ | 0 | 0 | 0 | 0 |

The experiments described in Tables 1–5 were then repeated, except that the amount of isopropanol was increased to 5%.

Table 6 depicts the results of experiments in which the amount of isopropanol in samples A1-F1 (Table 1) were increased to 5%.

TABLE 6

| Sample | A6 | B6 | C6 | D6 | E6 | F6 |
|---|---|---|---|---|---|---|
| % PCMX | 0 | .01 | .02 | .03 | .04 | .05 |
| % ISOPR | 5 | 5 | 5 | 5 | 5 | 5 |
| CFU/ml | $1 \times 10^7$ | $4 \times 10^6$ | $2 \times 10^6$ | $1.5 \times 10^6$ | $9 \times 10^5$ | $8 \times 10^5$ |

The number of CFU in samples A6-F6 were substantially the same (perhaps slightly less) than those exhibited by samples A1-F1.

Table 7 depicts the results of experiments in which the amount of isopropanol in samples, which otherwise correspond to samples A2-F2 (Table 2), was increased to 5%.

TABLE 7

| Sample | A7 | B7 | C7 | D7 | E7 | F7 |
|---|---|---|---|---|---|---|
| % PCMX | 0 | .01 | .02 | .03 | .04 | .05 |
| % CHX | .05 | .05 | .05 | .05 | .05 | .05 |
| % ISOPR | 5 | 5 | 5 | 5 | 5 | 5 |
| CFU/ml | $1 \times 10^6$ | $1.5 \times 10^5$ | $3.5 \times 10^4$ | $1.6 \times 10^3$ | 0 | 0 |

The data presented in Table 7 again demonstrates the synergistic relationship between CHX and PCMX. Further, the increase in the concentration of ISOPR from 2.5 to 5% seems to have slightly decreased the number of CFU. These results are further corroborated by data presented in Table 8, which relates to samples essentially the same as samples A3-F3 (Table 3), except that the amount of isopropanol was increased from 2.5 to 5%.

TABLE 8

| Sample | A8 | B8 | C8 | D8 | E8 | F8 |
|---|---|---|---|---|---|---|
| % PCMX | 0 | .01 | .02 | .03 | .04 | .05 |
| % CHX | .1 | .1 | .1 | .1 | .1 | .1 |
| % ISOPR | 5 | 5 | 5 | 5 | 5 | 5 |
| CFU/ml | $9 \times 10^5$ | $4.5 \times 10^4$ | $1.5 \times 10^3$ | 0 | 0 | 0 |

Table 9 presents the results of experiments in which the amount of isopropanol, in samples corresponding to samples A4-F4 (Table 4), was increased from 2.5% to 5%. A control sample for the samples set forth in Table 9, containing 5% ISOPR and no antimicrobial exhibited $1.2 \times 10^7$ CFU (not shown in Table 9).

TABLE 9

| Sample | A9 | B9 | C9 | D9 | E9 | F9 |
|---|---|---|---|---|---|---|
| % PCMX | 0 | .01 | .02 | .03 | .04 | .05 |
| % CHX | 0 | .05 | .05 | .05 | .05 | .05 |
| % BZK | .01 | .01 | .01 | .01 | .01 | .01 |
| % ISOPR | 5 | 5 | 5 | 5 | 5 | 5 |
| CFU/ml | $1.5 \times 10^6$ | $2.6 \times 10^2$ | 0 | 0 | 0 | 0 |

This data corroborates the synergistic relationship between CHX, PCMX, and BZK and further shows that an increase in the amount of isopropanol to 5% decreased CFU slightly. This conclusion is further supported by the results depicted in Table 10, where samples otherwise corresponding to samples A5-F5 (Table 5) contained 5%, rather than 2.5%, isopropanol.

TABLE 10

| Sample | A10 | B10 | C10 | D10 | E10 | F10 |
|---|---|---|---|---|---|---|
| % PCMX | 0 | .01 | .02 | .03 | .04 | .05 |
| % CHX | 0 | .05 | .05 | .05 | .05 | .05 |
| % BZK | .005 | .005 | .005 | .005 | .005 | .005 |
| % ISOPR | 5 | 5 | 5 | 5 | 5 | 5 |
| CFU/ml | $1.5 \times 10^6$ | $1.2 \times 10^3$ | 0 | 0 | 0 | 0 |

The synergistic effectiveness of low concentrations of CHX and PCMX (in 5% isopropanol) in the presence of blood was also demonstrated, as shown in Table 11.

TABLE 11

| Antimicrobial | CFU/ml |
| --- | --- |
| None (control) | $3 \times 10^6$ |
| .5% CHX | $1 \times 10^5$ |
| 1% CHX | $1 \times 10^4$ |
| .125% PCMX | $1 \times 10^6$ |
| .25% PCMX | $1.4 \times 10^4$ |
| .5% PCMX | 0 |
| .5% CHX + .25% PCMX | 0 |
| 1% CHX + .125% PCMX | 0 |

EXAMPLE

Comparison of Scrubs Prepared According to the Invention

The following antimicrobial scrubs were tested for antimicrobial effectiveness.

Scrub A. 3% PCMX
  1% phenoxyethanol
  10% propylene glycol
  10% pluronic F87
  1.8% lauryl dimethylamine oxide
  0.25% glucamate DOE 120
  1% D-gluconolactone
  73% deionized water Scrub B. Scrub A+0.1% BZK Scrub C. 3% PCMX
  5% isopropanol
  12.5% pluronic F87
  1.8% lauryl dimethylamine oxide
  0.25% glucamate DOE 120
  1.0% D-glucanolactone
  76.45% deionized water To assess antimicrobial effectiveness, 0.1 ml of each scrub was mixed with 0.9 ml of a culture of *Staphylococcus aureus* in TSB containing 10% serum, at $10^6$ CFU per ml. After 15 seconds, a 50 microliter aliquot was removed and diluted to 10 ml using drug inactivating medium (LTSB, see above), and 0.5 ml of the diluted culture was plated onto trypticase soy agar. After incubation at 37° C. for 24 hours, colony counts were determined, and the results are shown in Table 12.

TABLE 12

| Scrub | CFU/ml |
| --- | --- |
| A | 0 |
| B | 0 |
| C | $6 \times 10^3$ |
| HIBICLENS ® | $3 \times 10^4$ |
| TECHNICARE ® | $6 \times 10^5$ |
| ULTRADEX ® | $1 \times 10^5$ |
| Control | $3 \times 10^6$ |

EXAMPLE

Enhanced Activity in New Scrub Base

Various antimicrobial agents and compositions were combined in the following base (made to a volume of 100 ml with deionized water):
  5% isopropanol
  12.5% pluronic F87
  1.8% lauryl dimethylamine oxide
  0.25% glucamate DOE 120
  1.0% D-glucanolactone These compositions were tested for antimicrobial effectiveness using the same method set forth in Section 6, above. The results are shown in Table 13. The scrub base appeared to enhance the effectiveness of PCMX in particular.

TABLE 13

| Scrub Base + antimicrobial | CFU/ml |
| --- | --- |
| 2% chlorhexidine digluconate + 2% PCMX + 0.1% BZK | 0 |
| 2% PCMX | $1.2 \times 10^4$ |
| 3% PCMX | $6.0 \times 10^3$ |
| 2% chlorhexidine digluconate | $7.0 \times 10^4$ |
| 4% chlorhexidine digluconate | $1.0 \times 10^4$ |
| 0.1% BZK | $1.5 \times 10^6$ |
| 3% PCMX + 0.1% BZK | $5.0 \times 10^2$ |
| HIBICLENS ® | $3.0 \times 10^4$ |
| TECHNICARE ® | $6.0 \times 10^5$ |
| ULTRADEX ® | $1 \times 10^5$ |
| Control | $7.0 \times 10^6$ |

EXAMPLE

New Scrub Base With Propylene Glycol

Using the same methodology for antimicrobial testing set forth above, the effectiveness of the following scrub was tested, and compared to a commercially available scrub containing povidone iodine (BETADINE®, which contains 10 percent povidone iodine).

Scrub D:
  5% povidone iodine
  10% propylene glycol
  1% phenoxyethanol
  10% Pluronic F87
  1.8% lauryl dimethylamine oxide
  0.25% glucamate DOE 120
  1% D-gluconolactone
  71% deionized water

TABLE 14

| Scrub | CFU/ml |
| --- | --- |
| Scrub D | 0 |
| BETADINE ® | $3.0 \times 10^2$ |
| Control | $1.7 \times 10^6$ |

EXAMPLE

Scrub Comprising Polyhexamethylene Biguanide

Using the same methods set forth in example section 5, above, the rate of kill of compositions comprising PHMB, PCMX, BZK and PXE were tested. As demonstrated by Table 15, synergy was observed between BZK, PHMB, and PCMX at respective concentrations of 0.01%, 0.05%, and 0.05%. Synergy was also observed among 0.1% PXE+ 0.05% PHMB+0.05% PCMX.

TABLE 15

Rate of Kill of Polyhexamethylene (PHMB), Parachlorometaxylenol (PCMX), Benzalkonium Chloride (BZK), and Phenoxyethanol (PXE) Singly and in Combination vs *Staphyclococcus aureus*.

| ANTIMICROBIALS | CONCENTRATION % | CFU/mL |
|---|---|---|
| PHMB | 0.1 | $4.0 \times 10^6$ |
| PHMB | 0.05 | $2.0 \times 10^6$ |
| PHMB | 0.025 | $5.0 \times 10^6$ |
| PCMX | 0.1 | $1.6 \times 10^3$ |
| PCMX | 0.05 | $5.0 \times 10^6$ |
| PXE | 0.1 | $2.0 \times 10^7$ |
| BZK | 0.02 | $2.0 \times 10^7$ |
| PHMB + PCMX | 0.05 + 0.05 | $2.6 \times 10^4$ |
| PHMB + PCMX | 0.025 + 0.025 | $6.0 \times 10^5$ |
| PHMB + PCMX + BZK | 0.05 + 0.05 + 0.1 | $2.2 \times 10^3$ |
| PHMB + PCMX + PXE | 0.05 + 0.05 + 0.1 | $1.9 \times 10^3$ |
| PHMB + PCMX + PXE | 0.025 + 0.025 + 0.1 | $1.1 \times 10^5$ |
| Control | none | $2.0 \times 10^7$ |

EXAMPLE

Synergistic Efficacy of Biguanides, Triclosan, and Quaternary Ammonium Compounds Stock solutions of various combinations of antimicrobial agents were prepared so that 10-fold dilution would result in the concentrations set forth in Tables 16–20, below. 0.1 ml of the solutions were mixed with 0.9 ml of culture containing 107 CFU of *Staphylococcus aureus* per milliliter. The culture medium was 20 percent serum and 80 percent TSB. After a one minute exposure, the culture was diluted 100-fold with drug-inactivating medium (LTSB) and 0.2 ml was subcultured on a trypticase soy agar plate and incubated at 37° C. for 24 hours. The colony counts were then determined (Tables 16–20; CHX=chlorhexidine free base; PXE=phenoxyethanol; BZK=benzalkonium chloride).

TABLE 16

| Sample | A11 | B11 | C11 | D11 |
|---|---|---|---|---|
| % CHX | 0 | 0.025 | 0.05 | 0.1 |
| % Isopropanol | 5.0 | 5.0 | 5.0 | 5.0 |
| % PXE | 0.2 | 0.2 | 0.2 | 0.2 |
| Growth (CFU/ml) | $5 \times 10^7$ | $3 \times 10^7$ | $2 \times 10^7$ | $5 \times 10^6$ |

TABLE 17

| Sample | A12 | B12 | C12 | D12 |
|---|---|---|---|---|
| % CHX | 0 | 0.025 | 0.05 | 0.1 |
| % Triclosan | 0.025 | 0.025 | 0.025 | 0.025 |
| % Isopropanol | 5.0 | 5.0 | 5.0 | 5.0 |
| % PXE | 0.2 | 0.2 | 0.2 | 0.2 |
| Growth (CFU/ml) | $2 \times 10^7$ | $7 \times 10^5$ | $6 \times 10^4$ | $2 \times 10^3$ |

TABLE 18

| Sample | A13 | B13 | C13 | D13 |
|---|---|---|---|---|
| % CHX | 0 | 0.025 | 0.05 | 0.1 |
| % Triclosan | 0.05 | 0.05 | 0.05 | 0.05 |
| % Isopropanol | 5.0 | 5.0 | 5.0 | 5.0 |
| % PXE | 0.2 | 0.2 | 0.2 | 0.2 |
| Growth (CFU/ml) | $2 \times 10^6$ | $1 \times 10^5$ | $1 \times 10^4$ | 0 |

TABLE 19

| Sample | A14 | B14 | C14 | D14 |
|---|---|---|---|---|
| % CHX | 0 | 0.025 | 0.05 | 0.1 |
| % Triclosan | 0.1 | 0.1 | 0.1 | 0.1 |
| % Isopropanol | 5.0 | 5.0 | 5.0 | 5.0 |
| % PXE | 0.2 | 0.2 | 0.2 | 0.2 |
| Growth (CFU/ml) | $7 \times 10^2$ | 0 | 0 | 0 |

TABLE 20

| Sample | A15 | B15 | C15 | D15 | E15 |
|---|---|---|---|---|---|
| % CHX | 0 | 0.025 | 0.05 | 0.1 | 0.1 |
| % Triclosan | 0 | 0.05 | 0.05 | 0.05 | 0.025 |
| % BZK | 0.02 | 0.02 | 0.02 | 0.02 | 0.02 |
| % Isopropanol | 5.0 | 5.0 | 5.0 | 5.0 | 5.0 |
| % PXE | 0.2 | 0.2 | 0.2 | 0.2 | 0.2 |
| Growth (CFU/ml) | $5 \times 10^7$ | $5 \times 10^3$ | $1 \times 10^3$ | 0 | 0 |

EXAMPLE

Effectiveness Of Chlorinated Phenol-Containing Topical Cream

The following antiseptic compositions were prepared in SOFT SENSE® and evaluated for their effectiveness in rapidly inactivating pathogens.

Formulation A16: 0.05% triclosan +0.025% chlorhexidine gluconate+0.25% phenoxyethanol+0.005% benzalkonium chloride Formulation B16: 0.125% parachlorometaxylenol+0.025% chlorhexidine gluconate+0.25% phenoxyethanol+0.005% benzalkonium chloride Control: SOFT SENSE® only.

0.9 grams of each of the foregoing cream formulations were mixed with 0.1 ml of a liquid bacterial culture containing 106 CFU of *S.aureus* per milliliter. After 10 minutes, the cream was diluted 100-fold with drug-inactivating LTSB medium, and 0.5 ml was subcultured on a trypicase soy agar plate to determine colony counts. The results are set forth in Table 21, and show that even low concentrations of triclosan, used in combination with chlorhexidine, have effective antimicrobial activity.

TABLE 21

| Formulation | CFU/g cream |
|---|---|
| A16 | 0 |
| B16 | $6 \times 10^2$ |
| Control | $4 \times 10^5$ |

EXAMPLE

Surface Disinfectant Wipes

Surface disinfectant wipes were prepared by submerging cotton pads into one of the following formulations:

| | | |
|---|---|---|
| A17 | PHMB | 0.2% |
| | Triclosan | 0.1% |
| | BZK | 0.05% |
| | PXE | 0.1% |
| | Ethyl alcohol | 28% |
| | Isopropanol | 12% |
| | Water | 59.55% |
| B17 | PCMX | 0.2% |
| | Triclosan | 0.1% |
| | BZK | 0.05% |
| | PXE | 0.1% |
| | Ethyl alcohol | 28% |
| | Isopropanol | 12% |
| | Water | 59.55% |

The wipes were cut into 2 cm² pieces and mildly pressed for 6 seconds on trypticase soy agar plates seeded with 0.3 ml of $10^8$ CFU/ml of the following organisms, except for *Candida albicans*, for which the culture had $10^6$ CFU/ml. The wipes were removed, and the plates were incubated for 2 hours at 37° C., after which zones of inhibition were measured. As shown in Table 22, PHMB-impregnated wipes appeared to inhibit a wider spectrum of microorganisms compared to the PCMX-impregnated wipes.

TABLE 22

| | Zones of Inhibition | |
|---|---|---|
| Organism | A17(PHMB) | B17(PCMX) |
| S. aureus | 50 mm | 46 mm |
| P. aeruginosa | 25 mm | 0 |
| Enterobacter | 27 mm | 25 mm |
| E. coli | 33 mm | 30 mm |
| C. albicans | 32 mm | 27 mm |

EXAMPLE

Alcohol-Based Composition

The following composition may be used as a fast-acting disinfectant, e.g. for hands, i.v. insertion sites, and pre-operative preparation of the surgical site The antimicrobial activity of the following compositions was tested. A base was prepared from ethanol, methylcellulose (using a solution of 3% methylcellulose in water), and propylene glycol.

| Alcohol Base: | |
|---|---|
| ethanol | 70% |
| methylcellulose* | 20% |
| propylene glycol | 10% |

Using this base, compositions A18 and B18 were prepared as follows:

| A18 | |
|---|---|
| chlorhexidine gluconate | 0.05% |
| triclosan | 0.1% |
| benzalkonium chloride | 0.1% |
| B18 | |
| chlorhexidine gluconate | 0.05% |
| parachlorometaxylenol | 0.2% |
| benzalkonium chloride | 0.1% |

These compositions were tested for antimicrobial activity against *S. aureus*. To test each of the following compositions, a 0.1 ml aliquot of bacterial culture containing $10^7$ CFU/ml was spread on the surface of trpticase soy agar plates and, after 10 minutes, 0.3 ml of the following compositions were spread over the inoculated plates:

(1) A18 in alcohol base
(2) B18 in alcohol base
(3) PURELL® Hand Sanitizer (GOJO Industries)
(4) control—alcohol base only
(5) control—culture only PURELL® is a commercial product containing 60–70% alcohol, thickeners and emollients used for skin disinfection.

After 1 minute of contact between the lotion and the seeded agar, 2.7 ml of drug inactivating medium (LTSB) was added to each plate, mixed across the surface and removed. 0.1 ml of this extract, for each test, was diluted with 0.9 ml LTSB, and then 0.2 ml was subcultured to determine colony counts. The results are shown in Table 23.

TABLE 23

| Test Composition | CFU per PLATE |
|---|---|
| (1) A18 in alcohol base | 0 |
| (2) B18 in alcohol base | 0 |
| (3) PURELL ® Hand Sanitizer (GOJO Industries) | $1.9 \times 10^5$ |
| (4) control-alcohol base only | $5.0 \times 10^5$ |
| (5) control-culture only | $1.8 \times 10^6$ |

Various publications are cited herein, the contents of which are hereby incorporated by reference in their entireties.

What is claimed is:

1. An antimicrobial composition comprising (i) between 0.025 and 2 percent of an antimicrobial agent selected from the group consisting of chlorhexidine free base, a chlorhexidine salt, and polyhexamethylene biguanide; (ii) between 0.005 and 0.1 percent of benzalkonium chloride; and (iii) between 0.025 and 2 percent of a chlorinated phenol compound selected from the group consisting of parachlorometaxylenol and triclosan.

2. The composition of claim 1, wherein the chlorinated phenol compound is parachlorometaxylenol.

3. The composition of claim 1, wherein the chlorinated phenol compound is triclosan.

4. The composition of claim 3, wherein the antimicrobial agent is chlorhexidine free base.

5. The antimicrobial composition of claim 1 which is a cream.

6. The antimicrobial composition of claim 1 which is comprised in a disinfectant wipe.

7. A method of inhibiting the growth of bacteria on the skin of a subject in need thereof, comprising applying an effective amount of a composition according to claim 1 to said subject.

8. An antimicrobial composition comprising (i) between 0.05 and 0.1 percent of an antimicrobial agent selected from the group consisting of chlorhexidine free base, a chlorhexidine salt, and polyhexamethylene biguanide; (ii) between 0.005 and 0.1 percent of benzalkonium chloride; and (iii) between 0.025 and 0.1 percent of a chlorinated phenol compound selected from the group consisting of parachlorometoxylenol and triclosan.

9. The composition of claim 8, wherein the chlorinated phenol compound is parachlorometaxylenol.

10. The composition of claim 8, wherein the chlorinated phenol compound is triclosan.

11. The composition of claim 10, wherein the antimicrobial agent is chlorhexidine free base.

12. The antimicrobial composition of claim 8 which is a cream.

13. The antimicrobial composition of claim 8 which is comprised in a disinfectant wipe.

14. A method of inhibiting the growth of bacteria on the skin of a subject in need thereof, comprising applying an effective amount of a composition according to claim 8 to said subject.

15. The composition of claim 1, further comprising between 50 and 70 percent alcohol.

16. The composition of claim 8, further comprising between 50 and 70 percent alcohol.

* * * * *

UNITED STATES PATENT AND TRADEMARK OFFICE
CERTIFICATE OF CORRECTION

PATENT NO. : 6,503,952 B2
DATED : January 7, 2003
INVENTOR(S) : Modak et al.

It is certified that error appears in the above-identified patent and that said Letters Patent is hereby corrected as shown below:

Column 3,
Line 5, "hydroxynapthoate" should read -- hydroxynaphthoate --
Line 8, "1,1'hexamethyl-enebis" should read -- 1,1-'hexamethylene-bis --
Line 18, "alpha4" should read -- alpha-4 --

Column 4,
Line 41, "agent;" should read -- agents; --
Line 44, "salicvlic" should read -- salicylic --

Column 5,
Line 30, "cholrhexidine" should read -- chlorhexidine --

Column 9, Table 11,
"None (control)   3 × 10.sup.6" should read -- None (control)   3 × 10.sup.6 --;
"1% CHX           1 × 10.sup.4" should read -- 1% CHX           1 × 10.sup.4 --; and
".5% PCMX         0"            should read -- .5% PCMX         0 -- (underlined)

Column 11,
Table 15, "*Staphyclococcus*" should read -- *Staphylococcus* --

Column 12,
Line 46, "*S.aureus*" should read -- *S. aureus* --
Line 48, "trypicase" should read -- trypticase --

Column 13,
Line 67, "trpticase" should read -- trypticase --

UNITED STATES PATENT AND TRADEMARK OFFICE
CERTIFICATE OF CORRECTION

PATENT NO. : 6,503,952 B2
DATED : January 7, 2003
INVENTOR(S) : Modak et al.

It is certified that error appears in the above-identified patent and that said Letters Patent is hereby corrected as shown below:

<u>Column 14,</u>
Lines 58-59, "parachlorometoxylenol" should read -- parachlorometaxylenol --

Signed and Sealed this

Eighth Day of July, 2003

JAMES E. ROGAN
*Director of the United States Patent and Trademark Office*